United States Patent
Asmussen et al.

(10) Patent No.: US 6,548,510 B1
(45) Date of Patent: Apr. 15, 2003

(54) PHARMACEUTICAL COMPOSITION CONTAINING DEOXYPEGANINE FOR THE TREATMENT OF NICOTINE DEPENDENCE

(75) Inventors: Bodo Asmussen, Bendorf (DE); Thomas Hille, Neuwied (DE); Hans-Rainer Hoffmann, Neuwied (DE); Klaus Opitz, Münster (DE)

(73) Assignees: LTS Lohmann Therapie Systeme AG, Andernach (DE); HF Arzneimittelforschung GmbH, Werne (DE)

( * ) Notice: Subject to any disclaimer, the term of this patent is extended or adjusted under 35 U.S.C. 154(b) by 0 days.

(21) Appl. No.: 09/889,650

(22) PCT Filed: Feb. 8, 2000

(86) PCT No.: PCT/EP00/00975

§ 371 (c)(1), (2), (4) Date: Jul. 19, 2001

(87) PCT Pub. No.: WO00/48445

PCT Pub. Date: Aug. 24, 2000

(30) Foreign Application Priority Data

Feb. 19, 1999 (EP) .............................................. 19906979

(51) Int. Cl.⁷ ............................................. A61K 31/505
(52) U.S. Cl. ..................................... 514/267; 514/813
(58) Field of Search ......................................... 514/267

(56) References Cited

U.S. PATENT DOCUMENTS

| | | |
|---|---|---|
| 3,742,951 A | 7/1973 | Zaffaroni |
| 3,760,805 A | 9/1973 | Higuchi |
| 3,797,494 A | 3/1974 | Zaffaroni |
| 3,987,790 A | 10/1976 | Eckenhoff et al. |
| 3,996,934 A | 12/1976 | Zaffaroni |
| 4,031,894 A | 6/1977 | Urquhart et al. |
| 4,137,300 A | 1/1979 | Sheth et al. |
| 4,597,961 A | 7/1986 | Etscora |
| 4,769,028 A | 9/1988 | Hoffman et al. |
| 5,089,267 A | 2/1992 | Hille et al. |

FOREIGN PATENT DOCUMENTS

DE          36 29 304          10/1989

OTHER PUBLICATIONS

Database WPI Section Ch, Week 197913 Derwent Publications Ltd., London, GB; Class B02, AN 1979–25213B Telezhenet, Abstract, 1978.

Tulyaganov, et al, "The pharmacological characteristics of deoxypeganine hydrochloride," Farmakol. Toksikol. (Moscow) (1986), 49(3), pp. 37–40, Abstract.

CA 100:132532 Muratova, et al, "Toxicology of the new pharmaceutical preparation of dehydrooxypeganine hydrochloride" Med. Zh. Uzb. 1984, (1), 53–5 (abstract).

*Primary Examiner*—Rebecca Cook
(74) *Attorney, Agent, or Firm*—Frommer Lawrence & Haug LLP

(57) ABSTRACT

Desoxypeganine and its pharmaceutically acceptable acid addition salts are useful in treating nicotine dependence.

7 Claims, No Drawings

PHARMACEUTICAL COMPOSITION CONTAINING DEOXYPEGANINE FOR THE TREATMENT OF NICOTINE DEPENDENCE

This application is a 371 of PCT/EP00/00975 filed Feb. 8, 2000.

The present invention relates to the novel use of a little-known active compound for the treatment of nicotine dependence.

In particular, the present invention is directed at pharmaceutical use in formulations by means of which deoxypeganine or one of its pharmaceutically acceptable acid addition salts is delivered in a controlled, e.g. continuous, manner for the treatment of nicotine dependence.

Dependence on nicotine fulfils all of the criteria of drug dependence defined by the WHO:
- compulsive use
- psychoactive effects
- influence on the behavior
- stereotypical consumption habits
- abstinence symptoms on withdrawal or development of tolerance.

Smoking is thus not a "bad habit" and cannot be suppressed in all cases by willpower alone. Pharmacologists have found nicotine receptors in the brain which are a biological explanation for the fact that so many smokers relapse again and again in spite of strong motivation and good psychological support.

This knowledge led in 1975 to a completely new therapeutic approach, the supply of nicotine by chewing gum. Initially greeted enthusiastically, the system, however, very soon showed weak points. Thus, fault was found with the bitter taste and the low social acceptance of the chewing gum. Misuse in these systems also definitely occurs due to overdosage.

All these disadvantages led to the development of transdermal systems which contain nicotine, as are described, for example, in German Patent DE 36 29 304 and U.S. Pat. No. 4,597,961.

In the transdermal administration of nicotine, taste does not play a part, use is invisible, the release of the active compound takes place without substitutive oral gratification and plasma peaks are avoided.

Side effects observed are skin irritation at the application sites, reddening, slight swelling and itching, which in some cases led to the abandonment of the therapy.

A disadvantage of this nicotine therapy is moreover that in this type of treatment the extreme toxicity of the nicotine is not taken into account.

There is therefore a need for medicaments which safely suppress the symptoms of nicotine dependence without, however, the therapeutic doses of the active compound having a toxicity which is comparable to that of nicotine.

Up to now, substances from the following groups have been employed for the treatment of nicotine dependence:
- natural substances without nitrogen, e.g. γ-pyrones, citric acid, acetic acid, camphor, glucose, vitamins, terpenes and others
- alkaloids having a different spectrum of action, e.g. lobeline, caffeine, galanthamine and Apocynaceae alkaloids
- tricyclic antidepressants such as, for example, fluoxetine
- clonidine
- pyrrolopyrimidine It is recognized even from the different nature of the therapy principles that an effective medicament for the treatment of nicotine dependence has still not been found which is not as toxic as nicotine.

The object of the invention is therefore the provision of a pharmaceutical in an oral, transdermal or otherwise parenteral formulation which releases this pharmaceutical in a form which is as controlled as possible and guarantees that the desire for nicotine is decreased. The term parenterally should thus include all administration forms apart from oral administration, such as rectal, intravenous, intramuscular, intraperitoneal and nasal administration.

This object is achieved in a surprising manner according to the invention by the use of deoxypeganine and/or one of its pharmaceutically acceptable acid addition salts for the treatment of nicotine dependence.

This achievement is all the more surprising as deoxypeganine has in fact been investigated in detail in the former Soviet Union and its pharmacological actions have been intensively researched, but the use according to the invention of a deoxypeganine-containing formulation for the treatment of nicotine dependence has not been described up to now.

On account of its pharmacological properties, deoxypeganine belongs to the group of reversibly acting cholinesterase inhibitors, is closely related to physostigmine and neostigmine in its actions, but is distinguished by particular specific properties. Deoxypeganine as a matter of fact inhibits not only acetylcholinesterase, but also monoamine oxidase.

This advantage offsets its somewhat lower cholinesterase inhibitory action (in comparison to physostigmine) based on the unit of weight.

In contrast to neostigmine, deoxypeganine crosses the blood-brain barrier and antagonizes the cerebral actions of cholinergic toxins.

Deoxypeganine is obtained by isolation from the harmel peganum (Peganum harmala) or by synthesis.

Pharmaceutical forms which release active compounds in a controlled manner are already known in the prior art. The administration of pharmaceutically active compounds by means of such formulations can take place orally, transdermally or otherwise parenterally. In medicaments of this type, the deoxypeganine can be present as such or in the form of pharmaceutically acceptable acid addition salts, e.g. as a hydrohalide, in particular hydrochloride or hydrobromide, or as a salt of another pharmaceutically acceptable acid. These agents as a rule furthermore contain excipients, such as vehicles, flow-improving agents, solvents and oils, whose nature and amount varies depending on the presentation form. In general, the content of active compound in the medicament, calculated as free deoxypeganine, is between 0.1 and 50% by weight, preferably between 2 and 15% by weight.

Some formulations for oral administration suitable in the context of the present invention will be described briefly.

In such a formulation, the pharmaceutical active compound is encapsulated, for example, in a semipermeable membrane, such as, for example, in cellulose acetate. A tiny hole is drilled in the capsule material using a drill or laser. Water is absorbed by the capsule material in the body of the patient who is being treated. The pharmaceutical active compound is driven through the small opening by osmotic pressure in the desired gradual, constant and controlled manner. Such systems are described, for example, in U.S. Pat. No. 3,760,805 and U.S. Pat. No. 3,987,790. In these systems, the pharmaceutical active compounds can be present in solid form or absorbed on ion exchanger resins.

Another system for oral administration is described by Sheth and Leeson in U.S. Pat. No. 4,137,300. This patent describes a formulation which contains a wax matrix.

The active compounds of the present invention are administered in a fitting and suitable manner by means of appropriate formulations. The solid active compounds can be administered in solution or as a suspension. The solution or suspension medium can be aqueous or organic. Suitable solution or suspension media for deoxypeganine are, for example, water, silicone fluid or mineral oil.

In order to simplify the administration of a compound by means of a formulation as described above, a flow-improving agent can be added to the system. Some suitable flow-improving agents for oral formulations include, for example, polyethylene glycol, hydroxypropylmethylcellulose and sugar.

In a formulation for the transdermal administration of compounds according to the present invention, the pharmaceutical active compound can be contained in a matrix from which it is released in the desired gradual, constant and controlled manner. The permeability of the matrix during the release of the compound is based on diffusion. A system of this type is described in the German Patent 33 15 272 (U.S. Pat. No. 4,769,028). This system consists of an impermeable back layer, a specially constructed supersaturated active-compound reservoir associated therewith, made of a polymer matrix, a contact-adhesive layer permeable to the active compound, associated with the reservoir, and a protective layer covering the contact-adhesive layer, which can be removed again for use. Systems in which the reservoir layer has such a high intrinsic tackiness that it is simultaneously the contact-adhesive layer are also possible.

German Patent DE 38 43 239 (U.S. Pat. No. 5,089,267) describes such a system.

If the active compound is absorbed through the skin, the patient to be treated in this manner receives a controlled and predeterminable supply of the active compound.

Other suitable transdermal formulations are described in U.S. Pat. Nos. 3,742,951, 3,797,494, 3,996,934 and 4,031,894. These formulations fundamentally consist of a back layer which is one of the surfaces, an adhesive layer permeable to the active compound, which is the other surface, and finally a reservoir which contains the active compound between the two layers forming the surface. Alternatively to this, the active compound can also be contained in a multiplicity of microcapsules which are distributed in the permeable adhesive layer. In each case, the active compound is continuously released from the reservoir or the microcapsules by a membrane into the adhesive layer permeable to the active compound, which is in contact with the skin or mucous membrane of the patient to be treated. In the case of microcapsules, the capsule material can also act as a membrane.

Formulations which are suitable for the otherwise parenteral administration of deoxypeganine and its salts are those which make a depot action of the active compound possible. In this context, the formulation is applied as an injection solution on a nonaqueous basis. The possible solvents are known to the person skilled in the art. Examples which may be mentioned are the vegetable oils which individual pharmacopeias prescribe, such as peanut oil, olive oil, almond oil, sunflower oil, soybean oil and sesame oil. Castor oil often shows a particularly favorable solubility for medicaments; in addition oils of animal origin are also suitable.

The oils are physiologically indifferent and highly tolerable. The prerequisite for this is that they are specially purified and have low acid and peroxide counts. As intravenous administration is not possible because of the lack of miscibility with the blood serum and can lead to pulmonary embolism, their use is possible only for intramuscular and subcutaneous injection preparations. Oily solutions and suspensions remain at the site of administration for a very long time (often up to 1 month) and release the active compounds over a prolonged period.

The dose of deoxypeganine or its pharmaceutically acceptable acid addition salts must be so high and take place over such a long time that a lasting action is obtained, and needs individual adjustment.

The invention is illustrated by the following example:

Example: Influence of deoxypeganine on the smoking of healthy subjects

In the context of the testing of a deoxypeganine-containing formulation which releases about 50 mg of deoxypeganine hydrochloride per day in vivo, in addition to other subjects two smokers were also used as test subjects, as "smoking" was not an exclusion criterion in the testing. Surprisingly, in the two smokers the phenomenon occurred that the desire for cigarettes was obviously suppressed. The administration period was 24 hours. The data are shown in the following table:

TABLE 1

Influence of deoxypeganine HCl on smokers

|  | Cigarette consumption without deoxypeganine | Cigarette consumption after administration of 50 mg of deoxypeganine HCl/day |
| --- | --- | --- |
| Male subject | 22 cigarettes (x of n = 3)/day | 3 cigarettes |
| Female subject | 41 cigarettes (x of n = 5)/day | 6 cigarettes |

(x = mean value)

As the table shows, the single administration of 50 mg of deoxypeganine/day already caused a considerable reduction in cigarette consumption.

It can thus be ascertained that deoxypeganine and its pharmaceutically acceptable acid addition salts can be used for the treatment of nicotine dependence. These substances are preferably administered in a continuous and controlled manner. The pharmaceutical administration form makes controlled release possible for, for example, oral, transdermal or alternatively parenteral administration.

What is claimed is:

1. A method of treating nicotine dependence in a human being, which comprises administering an effective amount of an active agent selected from the group consisting of desoxypeganine and the pharmaceutically acceptable acid addition salts thereof to a human being in need thereof.

2. The method according to claim 1, wherein the active agent is administered as a composition suitable for oral, parenteral or transdermal administration.

3. The method according to claim 2, wherein the composition comprises an effective amount of the active agent and at least one pharmaceutically acceptable auxiliary.

4. The method according to claim 2, wherein said composition contains 0.1 to 50% by weight of the active agent, calculated as free desoxypeganine.

5. The method according to claim 2, wherein said composition contains 2 to 15% by weight of the active agent, calculated as free desoxypeganine.

6. The method according to claim 1, wherein the active agent is desoxypeganine hydrochloride.

7. The method according to claim 6, wherein the effective amount of desoxypeganine hydrochloride to be administered is about 50 mg per day.

* * * * *